United States Patent [19]

Chiarino et al.

[11] Patent Number: 5,145,872
[45] Date of Patent: Sep. 8, 1992

[54] PEPTIDES WITH PHARMACEUTICAL ACTIVITY

[75] Inventors: Dario Chiarino, Monza; Angelo Carenzi, Busto Arsizio; Davide Della Bella, Milan; Franco Pellacini, Sesto S. Giovanni, all of Italy

[73] Assignee: Zambon Group, S.p.A., Vicenza, Italy

[21] Appl. No.: 323,814

[22] Filed: Mar. 15, 1989

[30] Foreign Application Priority Data

Mar. 16, 1988 [IT] Italy ................... 19791 A/88

[51] Int. Cl.$^5$ .......................................... C07C 233/25
[52] U.S. Cl. ........................... 514/620; 514/18; 514/19; 530/331; 564/165
[58] Field of Search ............ 514/19, 18, 620; 530/331; 564/165

[56] References Cited

U.S. PATENT DOCUMENTS

| | | | |
|---|---|---|---|
| 4,029,547 | 6/1977 | Umezawa et al. | 195/80 R |
| 4,052,449 | 10/1977 | Umezawa et al. | 424/309 |
| 4,395,402 | 7/1983 | Umezawa et al. | 514/19 |
| 4,599,325 | 7/1986 | Hansen et al. | 514/19 |
| 4,883,808 | 11/1989 | Fodor et al. | |
| 4,894,392 | 1/1990 | Durette et al. | |
| 4,900,547 | 2/1990 | Levy et al. | |
| 4,933,179 | 6/1990 | Allison et al. | |
| 4,942,154 | 7/1990 | Durette et al. | |

FOREIGN PATENT DOCUMENTS 0236874 9/1987 European Pat. Off. .
2483409 7/1981 France .
0015256 2/1981 Japan ................... 514/18

OTHER PUBLICATIONS

Aoyagi et al., *J. Appl. Biochem.* 1984, vol. 6, pp. 212–221.
Poulson et al., ed. *Organic Chemistry*, 1980, pp. 1025–1031.
Talmadge et al., *13th Internatl. Congress of Chemotherapy*, 1983, pp. 203/19–203/35.
Journal of Medicinal Chemistry, vol. 20, No. 4. Apr. 1977.

*Primary Examiner*—Lester L. Lee
*Attorney, Agent, or Firm*—Stevens, Davis, Miller & Mosher

[57] ABSTRACT

Compounds of the formula

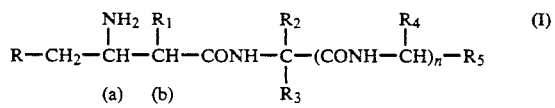

wherein R, $R_1$, $R_2$, $R_3$, $R_4$, $R_5$ and n have the meanings reported in the specification, processes for their preparation and pharmaceutical compositions containing them as active ingredient are described.

The compounds of formula I are inhibitor of enzymatic systems and they are useful in pharmaceutical field.

9 Claims, No Drawings

PEPTIDES WITH PHARMACEUTICAL ACTIVITY

The present invention relates to peptide compounds and to their reduction products with inhibitory activity of enzymatic systems and, more particularly, it relates to peptides of β-amino-butyric acid, to processes for their preparation and to pharmaceutical compositions containing them as active ingredient.

The drugs with activity on enzymatic systems represent a therapeutic class of recent development and of particular interest for its potential use in the pharmacological field in the treatment of immunodeficiency diseases, chronic infective diseases and diseases of tumoral origin.

Several natural as well as synthetic drugs have been studied; among these Levamisole (Merck Index 10th Ed., No. 9055, page 1321), Isoprinosin (Merck Index 10th Ed., No. 4859, page 722) and, more recently, Bestatin [Drug of the future, vol. VI, No. 10 (1981), page 604].

In particular, this last compound, whose chemical name is [(2S,3R)-3-amino-2-hydroxy-4-phenyl-butanoyl]-L-leucine, was isolated, the first time, from a culture of Streptomyces olivoreticuli (British Patent No. 1510323-Zaidan Hojin Biseibutsu). Afterwards, Bestatin has been extensively studied as far as the structure-activity relationship is concerned.

In the publication of R. Nishizawa and T. Saino, J. Med. Chem., vol. 20, (1977), No. 4, pages 510-515, the influence on the pharmacological activity of replacing L-leucine with other aminoacids was studied.

Among the different studied derivatives, only that having L-isoleucine showed an activity comparable with that of the parent molecule.

We have now surprisingly found that compounds in which the β-amino-α-phenylbutyric structure of Bestatin is substantially maintained but in which the second aminoacidic moiety is an α,α-disubstituted aminoacid, show not only an activity equal or superior to Bestatin but, in addition, they have further interesting pharmacological advantages.

Therefore object of the present invention are the compounds of formula

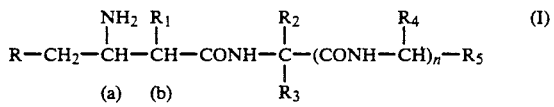

$$R-CH_2-\underset{(a)}{\overset{NH_2}{CH}}-\underset{(b)}{\overset{R_1}{CH}}-CONH-\underset{R_3}{\overset{R_2}{C}}-(CONH-\overset{R_4}{CH})_n-R_5 \qquad (I)$$

wherein

R represents a phenyl optionally substituted by from 1 to 3 substituents selected from hydroxy, halogen, $C_1$-$C_6$ alkoxy, $C_1$-$C_6$ alkyl, phenyl, amino, mono or dialkylamino groups having from 1 to 6 carbon atoms in the alkyl moiety, nitro, mercapto, alkylthio, alkylsulfinyl or alkylsulfonyl groups having from 1 to 6 carbon atoms in the alkyl moiety;

$R_1$ represents a hydroxy or mercapto group;

$R_2$ represents a linear or branched $C_1$-$C_6$ alkyl;

$R_3$ represents a linear or branched $C_1$-$C_6$ alkyl optionally substituted by a hydroxy, mercapto, $C_1$-$C_3$ alkylthio, amino, carboxy, ureido group;

or $R_2$ and $R_3$, together with the carbon atom to which they are bonded, represent a cycloalkylidene having from 3 to 8 carbon atoms optionally substituted by $C_1$-$C_3$ alkyl, $C_1$-$C_3$ alkoxy, hydroxy groups;

$R_4$ represents a hydrogen atom or a linear or branched $C_1$-$C_6$ alkyl optionally substituted by a hydroxy, mercapto, $C_1$-$C_3$ alkylthio, amino, carboxy, ureido group;

n represents 0 or 1;

$R_5$ represents a carboxy group or a group of formula $-COR_6$ wherein $R_6$ represents a $C_1$-$C_6$ alkoxy, an amino, mono or dialkylamino group having from 1 to 6 carbon atoms in the alkyl moiety; and when n=0 $R_5$ can be also a hydroxymethyl or a formyl group; the carbon atoms marked by (a) and (b) are in R or S configuration.

The compounds of formula I have an inhibitory activity of enzymatic systems and an immunostimulating activity and they are useful in therapy in the treatment of immunodeficiency disorders, diseases of tumoral origin, muscular dystrophy and in the enhancement of analgesia induced by opioids.

In particular, contrary to what reported in literature for related compounds [Takaaki Aoyagy et al., J. Appl. Biochem., 6, 212-221, (1984)], also the compounds of formula I wherein the carbon atom marked by (b) is in R configuration show interesting pharmacological properties, particularly a remarkable immunostimulating activity.

Preferred compounds of formula I are those wherein:

R represents a phenyl optionally substituted by a substituent selected from hydroxy, a chlorine, bromine or fluorine atom, a methoxy, ethoxy, ethyl, methyl, isopropyl, isobutyl, isopropoxy, isobutoxy, amino, nitro, phenyl, mercapto, methylthio, methylsulfinyl and methylsulfonyl group;

$R_1$ represents a hydroxy group;

$R_2$ represents methyl, ethyl, propyl, isopropyl, butyl, isobutyl, sec.butyl;

$R_3$ represents methyl, ethyl, propyl, isopropyl, butyl, isobutyl, sec.butyl, hydroxymethyl, hydroxyethyl, mercaptomethyl, methylthioethyl or $R_2$ and $R_3$, together with the carbon atom to which they are bonded, are a cyclopropylidene, cyclobutylidene, cyclopentylidene, cyclohexylidene;

n is 0 and $R_5$ represents carboxy.

The compounds of formula I can have one or more asymmetric centers, in addition to those marked by (a) and (b), and they can be in the form of stereoisomers.

Object of the present invention are the compounds of formula I in the form of stereoisomeric mixtures as well as in the form of single stereoisomers, preparable by separation from the stereoselective mixture according to conventional methods or by stereoselective synthesis.

A further object of the present invention are the salts of the compounds of formula I with pharmaceutically acceptable acids or, when $R_5$ represents a carboxy group or other acidic functions are present in the molecule, with pharmaceutically acceptable bases. Examples of suitable acids are hydrochloric, hydrobromic, benzoic, 4-hydroxybenzoic, tartaric, succinic, acetic, sulfuric, sulfonic, fumaric, hydriodic, glycolic, citric, maleic and phosphoric acid. Examples of suitable bases are sodium or potassium hydroxides, carbonates or bicarbonates, calcium hydroxide, ethanolamine, 2-hydroxymethyl-2-amino-1,3-propanediol, dimethylaminoethanol, benzathine, N-methyl-D-glucamine, ethylenediamine, arginine and lysine. A further object of the present invention are the processes for the preparation of the compounds of formula I.

The compounds of the present invention are prepared according to the following condensation reaction.

$$R-CH_2\underset{(a)}{-CH}\underset{(b)}{-CH}-COOH \;+\;$$
$$\overset{NH_2}{\phantom{R-CH_2-}}\overset{R_1}{\phantom{-CH-}}$$
(II)

$$H_2N-\underset{R_3}{\overset{R_2}{\underset{|}{\overset{|}{C}}}}-(CONH-\overset{R_4}{\underset{|}{CH}})_n-R_5 \longrightarrow (I)$$
(III)

wherein R, $R_1$, $R_2$, $R_3$, $R_4$, $R_5$ and n have the above reported meanings; the carbon atoms marked by (a) and (b) have R or S configuration. The compounds of formula II wherein R represents a phenyl substituted in 4 position by an alkylthio, alkylsulfinyl or alkylsulfonyl group and $R_1$ is a hydroxy group are new and they are a further object of the invention.

The reaction is carried out according to techniques known in peptide chemistry by first protecting the amino group of the compound of formula II and, then, by performing the condensation in the presence of a suitable condensing agent in an inert organic solvent, optionally in the presence of a base.

Suitable condensing agents are carbodiimides such as dicyclohexylcarbodiimide and 1-ethyl-3-(3-dimethylaminopropyl)-carbodiimide, optionally in the presence of N-hydroxy-benzotriazole.

The condensation reaction can be carried out also by using the mixed anhydride method, that is by preparing a mixed anhydride method between the carboxy group of the compounds of formula II and an ester of a suitable organic acid such as ethylchloroformate or isobutylchloroformate, or by using reactive esters of the compounds of formula II such as, for example, cyanomethyl esters, vinyl esters, substituted or unsubstituted phenyl esters, thiophenyl esters or esters of N-hydroxy-succinimide or N-hydroxyphthalimide.

For the condensation reaction, suitable organic solvents are ethers such as ethyl ether, tetrahydrofuran or dioxane, esters such as ethyl acetate, ketones such as acetone or methylethylketone, chlorinated hydrocarbons such as methylenechloride or chloroform, amides or nitriles such as dimethylformamide, dimethylacetamide or acetonitrile, or mixtures thereof.

Examples of suitable bases are inorganic bases such as sodium bicarbonate and magnesium oxide or organic bases such as triethylamine and N-methyl-morpholine.

Suitable protecting groups for the amino group are t.butoxycarbonyl and benzyloxycarbonyl or the amino nitrogen can be protected as imide, for example as phthalimide.

Alternatively, the compounds of formula I wherein n=1 can be prepared also by condensation of a suitably protected compound of formula II with an aminoacid of formula III (n=0, $R_5$=COOH) and by subsequent further condensation with an aminoacid of formula $$H_2N-\overset{R_4}{\underset{|}{CH}}-COOH \qquad (IV)$$

wherein $R_4$ has the above reported meanings.

It is clear to the man skilled in the art that before carring out the condensation reactions it can be optionally necessary to protect the carboxy group of the intermediates of formula III and IV.

The protection is carried out by esterification, for example with methanol, ethanol or with substituted or unsubstituted benzyl alcohol.

The removal of the protective groups to obtain the compounds of formula I is carried out according to usual methods in peptide chemistry for example by catalytic hydrogenation, by saponification with bases, by acid hydrolysis with hydrobromic acid in acetic acid, with trifluoroacetic acid, with hydrochloric acid in solvents such as dioxane, tetrahydrofuran or ethyl acetate or with hydrofluoric acid or by hydrazinolysis.

From the compounds of formula I wherein $R_5$=COOH, then, by esterification with a suitable alcohol or by amidation with ammonia or a suitable amine, the compounds of formula I wherein $R_5$ represents a $-COR_6$ group are obtained.

Finally, by reduction of the compounds of formula I wherein $R_5$=COOH or $-COR_6$ (n=0) the compounds of formula I wherein $R_5$ represents a hydroxymethyl ($-CH_2OH$) or a formyl (CHO) group are obtained.

Alternatively, the compounds of formula I wherein $R_5$ is a $COR_6$, $CH_2OH$ or CHO group can be prepared directly by reaction of a compound of formula II with an amine of formula III wherein $R_5$ is a $COR_6$, $CH_2OH$ or CHO group, by condensation under conditions similar to those above described.

The compounds of formula II wherein $R_1$=OH are known or easily preparable according to known methods such as, for example, the method described in the British Patent No. 1510477 (Zaidan Hojin Biseibutsu).

The compounds of formula II wherein $R_1$=SH are preparable from the corresponding compounds of formula II wherein $R_1$=OH according to known methods.

For example the secondary alcohol can be transformed, first, into a corresponding sulfonyloxy derivative, such as mesyloxy or tosyloxy, and then, by substitution with thioacetate, into the acetylthio derivative which gives the compounds of formula II wherein $R_1$=SH by simple hydrolysis. Such compounds can be also obtained directly from the intermediates II ($R_1$=OH) by treatment, for example, with diethylazodicarboxylate, triphenylphosphine and thioacetate.

Analogously the compounds of formula I wherein $R_1$=SH can be obtained according to one of the above described methods also from the corresponding compounds of formula I wherein $R_1$=OH.

The aminoacids of formula III wherein n=0, $R_5$=COOH, $R_2$ and $R_3$, together with the carbon atom to which they are bonded, are a cycloalkylidene are known [Can. J. Chem. 39, 1309, (1961)] or easily preparable according to known methods.

Examples of aminoacids of formula IV are glycine, alanine, valine, leucine, isoleucine, serine, norvaline, norleucine, threonine, cysteine, methionine, aspartic acid, glutamic acid, arginine and lysine.

As above reported, the compounds of formula I can have, in addition to the carbon atoms marked by (a) and (b) further asymmetric centers.

The single stereoisomers can be separated from the stereoisomeric mixture according to known techniques by fractional crystallization or by chromatography.

Alternatively the single stereoisomers can be prepared by stereoselective synthesis using intermediates wherein the asymmetric centers have predetermined configuration.

The salts of the compounds object of the present invention with pharmaceutically acceptable acids or bases are preparable according to conventional techniques.

The compounds of formula I object of the present invention are able to competitively inhibit important enzymatic systems such as leucylaminopeptidases which is involved in the catabolism of endogenous peptides in mammals, to modulate immuno responses and to enhance analgesia induced by opioids.

Surprisingly, the compounds of formula I, wherein the carbon atom marked by (b) is in R configuration, contrary to the 2R stereoisomers of Bestatin, are active and in particular show a remarkable immunostimulating activity.

These activities are equal or superior to that of Bestatin but the duration of activity is longer.

The activity as aminopeptidase inhibitor has been evaluated in vivo on analgesia induced by methionine-enkephalin (example 20). The compounds of formula I resulted to be more active than Bestatin. The antinociceptive effect after administration of the compounds of formula I resulted to be significantly longer than that of the control mice (treated only with methionine-enkephalin).

In addition, as it clearly appears from the data reported in example 20 (table 2), while Bestatin is not active when administered by intravenous route, the compounds object of the present invention maintain their activity of enhancing analgesia induced by opioids also when administered by systemic route.

This means that, contrary to Bestatin, the compounds of the invention are able to pass through the blood-brain barrier and they can be administered by systemic route.

The therapeutic uses of the compounds of formula I concern the treatment of pathologies which require an action on the immuno system such as those related to immunodepression or autoimmuno activity or in the presence of tumoral neoformations, preventing the appearance of muscular distrophies, inducing analgesia or enhancing the analgesia induced by an increased release of morphine-like endogenous peptides.

A further object of the present invention are the pharmaceutical compositions containing the compounds of formula I or their pharmaceutically acceptable salts as active ingredient.

These compositions can contain the active ingredient together with suitable pharmaceutical solid or liquid excipients and they can be administered by oral or parenteral route.

The doses of the compound of formula I will vary depending on the route of administration and the selected pharmaceutical preparation but they are between 10 mg and 1000 mg a day.

The pharmaceutical preparation, preparable according to conventional techniques, can be solid such as tablets, coated tablets, capsules, powders, granulates or liquid such as solutions, suspensions, emulsions.

In addition to the usual excipients, the compositions object of the present invention may contain also preserving agents, stabilizing agents, wetting agents, emulsifiers, salts in order to regulate the osmotic pressure, buffers, colouring agents, flavouring agents.

In order to better illustrate the present invention without limiting it, the following examples are now given.

EXAMPLE 1

1-[(2S,3R)-3-benzyloxycarbonylamino-2-hydroxy-4-(4-methylsulfonylphenyl)-butanoyl]-amino-1-cyclohexanecarboxylic acid benzyl ester 1-[(2S,3R)-3-benzyloxycarbonylamino-2-hydroxy-4-(4-methylsulfonylphenyl)]-butanoic acid (2 g; 0.0049 moles), 1-amino-1-cyclohexanecarboxylic acid benzyl ester p.toluenesulfonate (2.78 g; 0.00686 moles) and anhydrous 1-hydroxy-benzotriazole (0.73 g; 0.0054 moles) were suspended in a mixture of tetrahydrofuran (20 ml) and methylene chloride (5 ml).

Triethylamine (0.96 ml; 0.00686 moles) was added to the suspension, at room temperature and under stirring.

To the obtained solution dicyclohexylcarbodiimide (1.1 g; 0.0054 moles) dissolved in methylene chloride (5 ml) was added dropwise at 0° C. and under stirring.

The temperature was raised spontaneously to the room value and the solution was kept under stirring at this temperature for 3 days (72 hours).

The precipitated dicyclohexylurea was filtered.

The organic solution was evaporated to dryness, under reduced pressure.

The residue was dissolved in ethyl acetate and treated with 5% hydrochloric acid (twice), then with 5% sodium bicarbonate (twice) and finally with water.

The organic phase was separated, dried on sodium sulphate and evaporated to dryness under reduced pressure. The residue (3.3 g) was purified by chromatography on silica gel (70–230 mesh) with eluent ethyl acetate: petroleum ether=8:2.

1-[(2S,3R)-3-benzyloxycarbonylamino-2-hydroxy-4-(4-methylsulfonyl-phenyl)-butanoyl]-amino-1-cyclohexanecarboxylic acid benzyl ester (2 g; 65.5% yield) was obtained as a white crystalline solid with m.p. 140°–142° C.

$[\alpha]_D^{20} = +30.3°$ (c=1%, methanol)

$^1$H-NMR (200 MHz, CD$_3$OD-TMS): delta (ppm): 7.84−7.47 (m, 4H), 7.37−7.19 (m, 10H); $v_A$=5.11−$v_B$=5.05 (ABq, $J_{AB}$=12.5 Hz, 2H); $v_A$=4.95−$v_B$=4.85 (ABq, $J_{AB}$=12.6 Hz, 2H); 4.24 (m, 1H); 3.97 (d, 1H, J=2.6 Hz); 3.06 (s, 3H); 3.06−2.87 (m, 2H); 2.06−1.95 (m, 2H); 1.88−1.78 (m, 2H); 1.62−1.39 (m, 6H).

EXAMPLE 2

1-[(2S,3R)-3-benzyloxycarbonylamino-2-hydroxy-4-(4-methylsulfonyl-phenyl)-butanoyl]-amino-1-cyclopentanecarboxylic acid benzyl ester By working in a way similar to that described in example 1 and using [(2S,3R)-3-benzyloxycarbonylamino-2-hydroxy-4-(4-methylsulfonyl-phenyl)]-butanoic acid (10 g; 0.024 moles) and 1-aminocyclopentanecarboxylic acid benzyl ester p.toluenesulfonate (13.4 g; 0.0343 moles) as starting compounds, 1-[(2S,3R)-3-benzyloxycarbonylamino-2-hydroxy-4-(4-methylsulfonyl-phenyl)-butanoyl]-amino-1-cyclopentanecarboxylic acid benzyl ester was obtained (10 g; 68% yield) and used directly in the subsequent reaction.

An analytical sample was crystallized from acetonitrile - t.butylmethylether.

m.p. 165°–167° C.

$[\alpha]_D^{20} = +33.3°$ (c=1%, DMF)

$^1$H-NMR (200 MHz, CD$_3$OD-TMS): delta (ppm): 7.87−7.47 (m, 4H), 7.37−7.18 (m, 10H); $v_A$=5.14−$v_B$=5.10 (ABq, $J_{AB}$=12.4 Hz, 2H); $v_A$=4.97−$v_B$=4.88 (ABq, J=12.6 Hz, 2H); 4.24 (m, 1H); 3.98 (d, 1H, J=2.7 Hz); 3.07 (s, 3H); 3.09−2.85 (m, 2H); 2.29−2.07 (m, 2H); 2.02−1.87 (m, 2H); 1.77−1.65 (m, 4H).

By working in a similar way and starting from [(2S, 3R)-3-benzyloxycarbonylamino-2-hydroxy-4-(4-methylthiophenyl)]-butanoic acid (m.p.=174°–177° C.) the compound 1-[(2S,3R)-3-benzyloxycarbonylamino-2-hydroxy-4-(4-methylthio-phenyl)-butanoyl]-amino-1-cyclopentanecarboxylic acid benzyl ester was prepared.

EXAMPLE 3

1-[(2R,3S)-3-benzyloxycarbonylamino-2-hydroxy-4-(4-methylsulfonylphenyl)-butanoyl]-amino-1-cyclopentanecarboxylic acid benzyl ester By working in a way similar to that described in example 2 and using [(2R,3S)-3-benzyloxycarbonylamino-2-hydroxy-4-(4-methylsulfonyl-phenyl)]-butanoic acid (5.2 g; 0.012 moles) as starting compound, 1-[(2R,3S)-3-benzyloxycarbonylamino-2-hydroxy-4-(4-methylsulfonyl-phenyl)-butanoyl]-amino-1-cyclopentanecarboxylic acid benzyl ester was obtained (5.4 g; 70% yield) with m.p. 162°–164° C.

$[\alpha]_D^{20} = -32.6°$ (c=1%, DMF)

The H-NMR spectrum was identical with that of the enantiomer (2S,3R) described in example 2.

EXAMPLE 4

1-[(2S,3R)-3-benzyloxycarbonylamino-2-hydroxy-4-(4-methylsulfonyl-phenyl)-butanoyl]-amino-1-cyclobutanecarboxylic acid benzyl ester By working in a way similar to that described in Can. J. Chem. 39, 1309 (1961), 1-amino-1-cyclobutanecarboxylic acid benzyl ester p.toluenesulfonate with m.p. 169°–174° C. was prepared.

This compound (2.58 g; 0.00686 moles) was reacted with [(2S,3R)-3-benzyloxycarbonylamino-2-hydroxy-4-(4-methylsulfonyl-phenyl)]-butanoic acid (2 g; 0.0049 moles) in a way similar to that described in example 1.

A crude (2.9 g) was obtained and crystallized, first, from acetonitrile and, then, from ethanol giving 1[(2S, 3R)-3-benzyloxycarbonylamino-2-hydroxy-4-(4-methylsulfonyl-phenyl)-butanoyl]-amino-1-cyclobutanecarboxylic acid benzyl ester (1.74 g; 50% yield) as a white crystalline solid with m.p. 163°–165° C.

1H—NMR (200 MHz, CD$_3$OD-TMS): delta (ppm): 7.85−7.45 (m, 4H), 7.36−7.18 (m, 10H); $\nu_A$=5.15−$\nu_B$=5.11 (ABq, $J_{AB}$=12.4 Hz, 2H); $\nu_A$=4.95−$\nu_B$=4.88 (ABq, $J_{AB}$=12.6 Hz, 2H); 4.24 (m, 1H); 3.99 (d,1H, J=2.7 Hz); 3.06 (s, 3H); 3.08−2.84 (m, 2H); 2.68−2.46 (m, 2H); 2.35−2.15 (m, 2H); 2.04−1.84 (m, 2H).

EXAMPLE 5

1-[(2S,3R)-3-benzyloxycarbonylamino-2-hydroxy-4-(4-methylsulfonyl-phenyl)-butanoyl]-amino-1-cyclopropanecarboxylic acid benzyl ester By working in a way similar to that described in Can. J. Chem. 39, 1309, (1961), 1-amino-1-cyclopropanecarboxylic acid benzyl ester p.toluenesulfonate with m.p. 134°–140° C. was prepared. This compound (2.5 g; 0.0068 moles) was reacted with [(2S, 3R)-3-benzyloxycarbonylamino-2-hydroxy-4-(4-methylsulfonyl-phenyl)]-butanoic acid (2 g; 0.0049 moles) in a way similar to that described in example 1.

A crude (2 g) was obtained and purified by chromatography on silica gel (eluent ethyl acetate; petroleum ether=8:2) giving 1-[(2S, 3R)-3-benzyloxycarbonylamino-2-hydroxy-4-(4-methylsulfonylphenyl)-butanoyl]-amino-1-cyclopropanecarboxylic acid benzyl ester (1 g; 35.15% yield) with m.p. 184°–186° C.

$[\alpha]_D^{20} = +39.7°$ (c=1%, DMF) 1H-NMR (200 MHz, CD$_3$OD-TMS): delta (ppm): 7.84−7.48 (m, 4H), 7.36−7.18 (m, 10H); 5.08 (s, 2H); $\nu_A$=4.94−$\nu_B$=4.86 (ABq, $J_{AB}$=12.6 Hz, 2H); 4.21 (m, 1H); 4.02 (d, 1H, J=2.7 Hz); 3.06 (s, 3H); 3.08−2.83 (m, 2H); 1.50−1.45 (m, 2H); 1.10−1.03 (m, 2H).

EXAMPLE 6

N-[(2S,3R)-3-benzyloxycarbonylamino-2-hydroxy-4-(4-methylsulfonyl-phenyl)-butanoyl]-α-methyl-alanine benzyl ester By working in a way similar to that described in example 1 and using [(2S,3R)-3-benzyloxycarbonylamino-2-hydroxy-4-(4-methylsulfonyl-phenyl)]-butanoic acid (3 g; 0.00736 moles) and α-methylalanine benzyl ester p.toluenesulfonate (3.96 g; 0.0102 moles) as starting compounds, a crude (4 g) was obtained and purified by chromatography on silica gel (eluent ethyl acetate: petroleum ether=8:2) and subsequently by crystallization from a mixture of t.butylmethylether: acetonitrile=85:15.

N-[(2S,3R)-3-benzyloxycarbonylamino-2-hydroxy-4-(4-methylsulfonyl-phenyl)-butanoyl]-α-methyl-alanine (1.16 g; 27% yield) was obtained as a solid with m.p. 146°–147° C.

$[\alpha]_D^{20} = +37.3°$ (c=1%, DMF)

1H-NMR (200 MHz, CD$_3$OD-TMS): delta (ppm): 7.84−7.46 (m, 4H), 7.32−7.19 (m, 10H); $\nu_A$=5.12−$\nu_B$=5.08 (ABq, $J_{AB}$=12.4 Hz, 2H); $\nu$=4.94−$\nu_B$=4.87 (ABq, $J_{AB}$=12.6 Hz, 2H); 4.23 (m, 1H); 3.95 (d, 1H, J=2.7 Hz); 3.06 (s, 3H); 3.06−2.85 (m, 2H); 1.43 (s, 6H).

EXAMPLE 7

1-[(2S,3R)-3-benzyloxycarbonylamino-2-hydroxy-4-phenyl-butanoyl]-amino-1-cyclopentanecarboxylic acid benzyl ester By working in a way similar to that described in example 2 and using (2S,3R)-3-benzyloxycarbonylamino-2-hydroxy-4-phenyl-butanoic acid (5 g; 0.015 moles) as starting compound, 1-[(2S,3R)-3-benzyloxycarbonylamino-2-hydroxy-4-phenyl-butanoyl]-amino-1-cyclopentanecarboxylic acid benzyl ester (5.1 g; 63% yield) with m.p. 133°–135° C. (isopropyl acetate) was obtained.

$[\alpha]_D^{20} = +23.9°$ (c=1, DMF)

1H-NMR (200 MHz, DMSO-d$_6$+D$_2$O-TMS): delta (ppm): 8.06 (s, 1H); 7.36−7.13 (m, 15H), 6.83 (d, J=9.3 Hz, 1H); $\nu_A$=5.05−$\nu_B$=4.98 (ABq, $J_{AB}$=13.3 Hz, 2H); $\nu_A$=4.90−$\nu_B$=4.85 (ABq, $J_{AB}$=13 Hz, 2H); 4.09−3.93 (m, 1H); 3.83 (d, J=3.2 Hz, 1H); $\nu_A$=2.80−$\nu_B$=2.64 (AB portion of an ABX system, $J_{AB}$=13.5 Hz, $J_{AX}$=6.3 Hz, $J_{BX}$=8.7 Hz, 2H); 2.10−1.77 (m, 4H); 1.72−1.42 (m, 4H).

EXAMPLE 8

1-[(2S,3R)-3-amino-2-hydroxy-4-(4-methylsulfonyl-phenyl)-butanoyl]-amino-1-cyclohexanecarboxylic acid (Compound 1)

To a solution of 1-[(2S,3R)-3-benzyloxycarbonylamino-2-hydroxu-4-(4-methylsulfonyl-phenyl)-butanoyl]-amino-1-cyclohexanecarboxylic acid benzyl ester (1.8 g; 0.0029 moles), prepared as described in example 1, in acetic acid (20 ml), 10% palladium on charcoal (0.2 g) was added under nitrogen.

The suspension was hydrogenated under pressure (2-3 atm) in a Parr apparatus and filtered on celite after the end of hydrogen absorption.

The filtrate was evaporated to dryness under reduced pressure and the residue was dissolved in water and evaporated again to completely remove acetic acid. The crude was triturated in acetone, filtered and dried under vacuo at 60° C.

1-[(2S,3R)-3-amino-2-hydroxy-4-(4-methylsulfonyl-phenyl)-butanoyl]-amino-1-cyclohexanecarboxylic acid (0.91 g; 79% yield) was obtained with m.p. 222°-224° C. (dec.). $[\alpha]_D^{20} = +55.5°$ (c=1%, HCl 0.1N) $^1$H-NMR (200 MHz, DCl 1N in D$_2$O-TSP): delta (ppm): 7.98−7.61 (m, 4H); 4.31 (d, 1H, J=4.8 Hz); 3.90 (m, 1H); 3.27 (s, 3H); $\nu_A$=3.28−$\nu_B$=3.14 (AB portion of an ABX system, $J_{AB}$=14.3 Hz, $J_{AX}$=7.0 Hz, $J_{BX}$=8.5 Hz, 2H); 2.05−1.94 (m, 2H); 1.88−1.76 (m, 2H); 1.67−1.25 (m, 6H).

EXAMPLE 9

1-[(2S,3R)-3-amino-2-hydroxy-4-(4-methylsulfonyl-phenyl)-butanoyl]-amino-1-cyclopentanecarboxylic acid (Compound 2)

1-[(2S,3R)-3-benzyloxycarbonylamino-2-hydroxy-4-(4-methylsulfonyl-phenyl)-butanoyl]-amino-1-cyclopentanecarboxylic acid benzyl ester (10.1 g; 0.0166 moles), prepared as described in example 2, was hydrogenated by working in a way similar to that described in example 8, obtaining 1-[(2S,3R)-3-amino-2-hydroxy-4-(4-methylsulfonyl-phenyl)-butanoyl]-amino-1-cyclopentanecarboxylic acid (3.6 g; 56.4% yield) with m.p. 226°-228° C. (dec.).

$[\alpha]_D^{20} = -4.4°$ (c=1%, HCl 0.1N)

$^1$H-NMR (200 MHz, DCl 1N in D$_2$O-TSP): delta (ppm): 7.97−7.60 (m, 4H); 4.26 (d, 1H, J=4.7 Hz); 3.91 (m, 1H); 3.27 (s, 3H); $\nu_A$=3.27−$\nu_B$=3.15 (AB portion of an ABX system, $J_{AB}$=14.3 Hz, $J_{AX}$=6.9 Hz, $J_{BX}$=7.9 Hz, 2H); 2.26−2.13 (m, 2H); 2.02−1.86 (m, 2H); 1.80−1.67 (m, 4H).

EXAMPLE 10

1-[(2R,3S)-3-amino-2-hydroxy-4-(4-methylsulfonyl-phenyl)-butanoyl]-amino-1-cyclopentanecarboxylic acid (Compound 3)

1-[(2R,3S)-3-benzyloxycarbonylamino-2-hydroxy-4-(4-methylsulfonyl-phenyl)-butanoyl]amino-1-cyclopentanecarboxylic acid benzyl ester (4 g; 0.0056 moles), prepared as described in example 3, was hydrogenated by working in a way similar to that described in example 8, obtaining 1-[(2R,3S)-3-amino-2-hydroxy-4-(4-methylsulfonyl-phenyl)-butanoyl]-amino-1-cyclopentanecarboxylic acid (1.56 g; 72% yield) with m.p. 226°-228° C. (dec.).

$[\alpha]_D^{20} = +4.2°$ (c=1%, HCl 0.1N)

The $^1$H-NMR spectrum was identical with that of the enantiomer (2S,3R) described in example 9.

EXAMPLE 11

1-[(2S,3R)-3-amino-2-hydroxy-4-(4-methylsulfonyl-phenyl)-butanoyl]-amino-1-cyclobutanecarboxylic acid (Compound 4)

1-[(2S,3R)-3-benzyloxycarbonylamino-2-hydroxy-4-(4-methylsulfonyl-phenyl)-butanoyl]-amino-1-cyclobutanecarboxylic acid benzyl ester (1 g; 0.00168 moles), prepared as described in example 4, was hydrogenated by working in a way similar to that described in example 8, obtaining 1-[(2S,3R)-3-amino-2-hydroxy-4-(4-methylsulfonyl-phenyl)-butanoyl]-amino-1-cyclobutanecarboxylic acid (0.5 g; 80% yield) with m.p. 247°-249° C. (dec.).

$[\alpha]_D^{20} = -12.1°$ (c=1%, HCl 0.1N)

$^1$H—NMR (200 MHz, DCl 1N in D$_2$O-TSP): delta (ppm): 8.00−7.61 (m, 4H); 4.27 (d, 1H, J=4.4 Hz); 3.94 (m, 1H); 3.27 (s, 3H); $\nu_A$=3.29−$\nu_B$=3.18 (AB portion of an ABX system, $J_{AB}$=14.4 Hz, $J_{AX}$=7.3 Hz, $J_{BX}$=7.7 Hz, 2H); 2.73−2.52 (m, 2H); 2.42−2.17 (m, 2H); 2.92−2.13 (m, 2H).

EXAMPLE 12

1-[(2S,3R)-3-amino-2-hydroxy-4-(4-methylsulfonyl-phenyl)-butanoyl]-amino-1-cyclopropanecarboxylic acid (Compound 5)

1-[(2S,3R)-3-benzyloxycarbonylamino-2-hydroxy-4-(4-methylsulfonyl-phenyl)-butanoyl]-amino-1-cyclopropanecarboxylic acid benzyl ester (0.9 g; 0.0015 moles), prepared as described in example 5, was hydrogenated by working in a way similar to that described in example 8, obtaining 1-[(2S,3R)-3-amino-2-hydroxy-4-(4-methylsulfonyl-phenyl)-butanoyl]-amino-1-cyclopropanecarboxylic acid (0.311 g; 58.2% yield) with m.p. 256°-258° C.

$^1$H-NMR (200 MHz, DCl 1N in D$_2$O-TSP): delta (ppm): 7.99−7.61 (m, 4H); 4.25 (d, 1H, J=3.7 Hz); 3.99 (m, 1H); 3.27 (m, 3H); $\nu_A$=3.29−$\nu_B$=3.20 (AB portion of an ABX system, $J_{AB}$=14.2 Hz, $J_{AX}$=7.5 Hz, $J_{BX}$=7.7 Hz, 2H); 1.65−1.50 (m, 2H); 1.30−1.13 (m, 2H).

EXAMPLE 13

N-[(2S,3R)-3-amino-2-hydroxy-4-(4-methylsulfonyl-phenyl)-butanoyl]-α-methyl-alanine (Compound 6)

N-[(2S,3R)-3-benzyloxycarbonylamino-2-hydroxy-4-(4-methylsulfonyl-phenyl)-butanoyl]-α-methyl-alanine benzyl ester (1 g; 0.0017 moles), prepared as described in example 6, was hydrogenated by working in a way similar to that described in example 8, obtaining N-[(2S,3R)-3-amino-2-hydroxy-4-(4-methylsulfonyl-phenyl)-butanoyl]-α-methyl-alanine (0.42 g; 69% yield) with m.p. 220°-222° C. $^1$H-NMR (200 MHz, DCl 1N in D$_2$O-TSP): delta (ppm): 8.01−7.61 (m, 4H); 4.25 (d, 1H, J=4.4 Hz); 3.93 (m, 1H); 3.28 (s, 3H); $\nu_A$=3.28−$\nu_B$=3.16 (AB portion of an ABX system, $J_{AB}$=14.4 Hz, $J_{AX}$=6.6 Hz, $J_{BX}$=8.1 Hz, 2H); 1.51 (s, 3H); 1.48 (s, 3H).

EXAMPLE 14

1-[(2S,3R)-3-amino-2-hydroxy-4-phenylbutanoyl]-amino-1-cyclopentanecarboxylic acid (Compound 7)

1-[(2S,3R)-3-benzyloxycarbonylamino-2-hydroxy-4-phenylbutanoyl]-amino-1-cyclopentanecarboxylic acid benzyl ester (4.5 g; 0.0085 moles), prepared as described in example 7, was hydrogenated by working in a way similar to that described in example 8, obtaining 1-[(2S,3R)-3-amino-2-hydroxy-4-phenylbutanoyl]-amino-1-cyclopentanecarboxylic acid (2.6 g; 84% yield) with m.p. 224°-225° C.

$[\alpha]_D^{20} = -31.4°$ (c=1%, acetic acid)

$^1$H-NMR (200 MHz, DCl 1N in D$_2$O-TSP): delta (ppm): 7.53−7.35 (m, 5H); 4.31 (d, J=5.1 Hz, 1H); 3.91−3.79 (m, 1H); $\nu_A$=3.19−$\nu_B$=3.01 (AB portion of an ABX system, $J_{AB}$=14.3 Hz, $J_{AX}$=6.4 Hz, $J_{BX}$=8.7

Hz, 2H); 2.35−2.17 (m, 2H); 2.11−1.91 (m, 2H); 1.87−1.74 (m, 4H).

EXAMPLE 15

1-[(2S,3R)-3-benzyloxycarbonylamino-2-hydroxy-4-(4-methylsulfonyl-phenyl)-butanoyl]-amino-1-cyclopentanecarboxylic acid 1-[(2S,3R)-3-amino-2-hydroxy-4-(4-methylsulfonyl-phenyl)-butanoyl]-amino-1-cyclopentanecarboxylic acid (2 g; 0.0052 moles), prepared as described in example 9, was dissolved in a solution of NaOH 0.1N (52 ml). To the so obtained solution a solution of benzylchloroformate (1 ml; 0.0062 moles) in ethyl acetate (10 ml) and, simultaneously, a solution of NaOH 0.5N in order to keep a basic pH were added dropwise. The addition was carried out at +10° C. and under stirring.

At the end of the addition the temperature of the reaction mixture was raised spontaneously to the room value. The phases were separated; the aqueous phase was acidified with hydrochloric acid up to pH 1 and then it was treated with ethyl acetate (2×50 ml). The collected organic phases were dried on sodium sulfate and evaporated to dryness.

The residue was crystallized from methanol giving 1-[(2S,3R)-3-benzyloxycarbonylamino-2-hydroxy-4-(4-methylsulfonyl-phenyl)-butanoyl]-amino-1-cyclopentanecarboxylic acid (1.5 g; 56% yield) with m.p. 127°-130° C. (dec.).

$[\alpha]_D^{20} = +40.5°$ (C=1%, DMF)

$^1$H—NMR (200 MHz, DMSO-$d_6$+$D_2O$-TMS): delta (ppm): 7.92 (s, 1H); 7.84−7.43 (m, 4H); 7.33−7.14 (m, 5H); 6.95 (d, J=9.51 Hz, 1H); $\nu_A$=4.90−$\nu_B$=4.84 (ABq, $J_{AB}$=12.86 Hz, 2H); 4.12−3.97 (m, 1H); 3.85 (d, J=3.4 Hz, 1H); 3.14 (s, 3H); $\nu_A$=2.94−$\nu_B$=2.77 (AB portion of an ABX system, $J_{AB}$=13.58 Hz, $J_{AX}$=5.31 Hz, $J_{BX}$=9.43 Hz, 2H); 2.07−1.78 (m, 4H); 1.70−1.52 (m, 4H).

EXAMPLE 16

N$^\alpha$-[1-[(2S,3R)-3-benzyloxycarbonylamino-2-hydroxy-4-(4-methylsulfonyl-phenyl)-butanoyl]-amino-1-cyclopentanecarbonyl]-N$^\omega$-benzyloxycarbonyl-L-arginine benzyl ester By working in a way similar to that described in example 1 and using 1-[(2S,3R)-3-benzyloxycarbonylamino-2-hydroxy-4-(4-methylsulfonyl-phenyl)-butanoyl]-amino-1-cyclopentanecarboxylic acid (0.4 g; 0.00077 moles), prepared as described in example 15, and N$^\omega$-benzyloxycarbonyl-L-arginine benzyl ester (0.614 g; 0.00154 moles) as starting compounds, N$^\alpha$-[1-[(2S,3R)-3-benzyloxycarbonylamino-2-hydroxy-4-(4-methylsulfonyl-phenyl)-butanoyl]-amino-1-cyclopentanecarbonyl]-N$^\omega$-benzyloxycarbonyl-L-arginine benzyl ester was obtained (0.207 g; 30% yield).

$[\alpha]_D^{20} = +9.15°$ (c=1%, DMF)

$^1$H-NMR (200 MHz, DMSO-$d_6$+$D_2O$-TMS): delta (ppm): 7.82−7.46 (m, 5H); 7.33−7.14 (m, 15H); $\nu_A$=4.92−$\nu_B$=4.81 (ABq, $J_{AB}$=12.8 Hz, 2H); 4.26 (m, 1H); 4.06 (m, 1H); 3.87 (d, J=2.7 Hz, 1H); 3.12 (s, 3H); 3.10−2.75 (m, 4H); 2.16−2.00 (m, 1H); 1.91−1.33 (m, 12H).

EXAMPLE 17

N$^\alpha$-[1-[(2S,3R)-3-amino-2-hydroxy-4-(4-methylsulfonyl-phenyl)butanoyl]-amino-1-cyclopentanecarbonyl]-L-arginine (Compound 8)

N$^\alpha$-[1-[(2S,3R)-3-benzyloxycarbonylamino-2-hydroxy-4-(4-methylsulfonyl-phenyl)-butanoyl]-amino-1-cyclopentanecarbonyl]-N$^\omega$-benzyloxycarbonyl-L-arginine benzyl ester (0.180 g; 0.0002 moles), prepared as described in example 16, was hydrogenated by working in a way similar to that described in example 8, obtaining N$^\alpha$-[1-[(2S,3R)-3-amino-2-hydroxy-4-(4-methylsulfonyl-phenyl)-butanoyl]-amino-1-cyclopentanecarbonyl]-L-arginine (0.085 g; 79% yield) with m.p. 142°-145° C.

$[\alpha]_D^{20} = +1.6°$ (c=1%, DMF)

$^1$H-NMR (200 MHz, DCl 1N in $D_2O$-TSP): delta (ppm): 8.03−7.66 (m, 4H); 4.45−4.38 (m, 1H); 4.34 (d, J=5 Hz, 1H); 4.04−4.94 (m, 1H); 3.31 (s, 3H); 3.28−3.12 (m, 4H); 2.24−1.60 (m, 12H).

EXAMPLE 18

N-(1-hydroxymethyl-1-cyclohexyl)-(2S, 3R)-3-benzyloxycarbonylamino-2-hydroxy-4-(4-methylsulfonylphenyl)-butanamide By working in a way similar to that described in Tetrahedron Letters, 40, 3527-3528, (1977), (1-amino-1-cyclohexyl)-methanol tosylate with m.p. 160°-161° C. was prepared.

By working in a way similar to that described in example 1 and using [(2S, 3R)-3-benzyloxycarbonylamino-2-hydroxy-4-(4-methylsulfonyl-phenyl)]-butanoic acid (1.55 g; 0.0038 moles) and (1-amino-1-cyclohexyl)-methanol tosylate (1.14 g; 0.0038 moles) as starting compounds, N-(1-hydroxymethyl-1-cyclohexyl)-(2S, 3R)-3-benzyloxycarbonylamino-2-hydroxy-4-(4-methylsulfonyl-phenyl)-butanamide (0.35 g; 23% yield) was obtained as an oil.

$^1$H—NMR (200 MHz, DMSO-$d_6$+$D_2O$-TMS): delta (ppm): 7.82−7.47 (m, 4H); 7.36−7.14 (m, 5H); 7.01 (d, J=9.7 Hz, 1H); 6.86 (s, 1H); $\nu_A$=4.90 −$\nu_B$=4.82 (ABq, $J_{AB}$=13 Hz, 2H); 4.18−4.02 (m, 1H); 3.81 (d, J=2.53 Hz, 1H); 3.13 (s, 3H); $\nu_A$=3.44−$\nu_B$=3.30 (ABq, $J_{AB}$=10.85 Hz, 2H); $\nu_A$=2.92−$\nu_B$=2.80 (AB portion of an ABX system, $J_{AB}$=13.60 Hz, $J_{AX}$=5.47 Hz, $J_{BX}$=9.40 Hz, 2H); 2.02−1.83 (m, 2H); 1.46−1.07 (m, 8H).

EXAMPLE 19

N-(1-hydroxymethyl-1-cyclohexyl)-(2S, 3R)-3-amino-2-hydroxy-4-(4-methylsulfonyl-phenyl)-butanamide hydrochloride (Compound 9)

N-(1-hydroxymethyl-1-cyclohexyl)-(2S, 3R)-3-benzyloxycarbonyl-2-hydroxy-4-(4-methylsulfonyl-phenyl)-butanamide (0.30 g; 0.0074 moles), prepared as described in example 18, was hydrogenated by working in a way similar to that described in example 8. The obtained compound was dissolved in methanolic hydrochloric acid 10N and the solution was evaporated to dryness under reduced pressure giving N-(1-hydroxymethyl-1-cyclohexyl)-(2S, 3R)-3-amino-2-hydroxy-4-(4-methylsulfonyl-phenyl)-butanamide hydrochloride (0.163 g; 73% yield) with m.p. 132°-135° C.

$[\alpha]_D^{20} = +6.9°$ (c=1%, DMF)

$^1$H—NMR (200 MHz, DCl 1N-TMS): delta (ppm): 7.97−7.63 (m, 4H); 4.50 (d, J=3.0 Hz, 1H);

$v_A=4.41-v_B=4.30$ (ABq, $J_{AB}=12.27$ Hz, 2H); 4.18−4.10 (m, 1H); 3.26 (s, 3H); 3.28−3.22 (m, 2H); 1.85−1.36 (m; 10H).

EXAMPLE 20

In vivo evalutation of the activity on methionine-enkephalin-induced analgesia Male Swiss mice (CD Charles River) weighing 22-24 g received intracerebroventricular (i.c.v.) injection of methionineenkephalin as described by Haley and Mc Cormick [Br. J. Pharmacol., 12, 12–15, (1957)].

Methionine-enkephalin was dissolved in distilled water and microinjected in a volume of 10 μl/mouse and in a dose analgesic in less than 30% of animals. The dose (10.25 or 50 μg/mouse) was chosen at the beginning of each experience depending on each batch's analgesic activity.

The antinociceptive effect was tested by the hot plate test as described by Eddy and Leimbach [(J. Pharmacol. Exptl. Therap., 107, 385-393, (1953)]. The time in seconds from contact with the plate (51.5° C.) to paw licking or Jumping accurrence was recorded as the response latency.

Animals were removed as soon as they reacted or after 30 seconds if they at 3, 6, 9, 12 and 15 minutes after the i.c.v. treatment and the latency times measured were used to calculate the reaction time areas. At first the compounds of formula I and Bestatin were administered simultaneously to methionine-enkephalin (dissolved in the same solution) by intracerebroventricular treatment to evaluate their activity without any interference due to absorbtion or diffusion through the blood-brain barrier.

In table 1 the results obtained for some representative compounds of formula I in comparison with Bestatin are reported.

The results reported in table 1 and 2 show that the compounds of formula I are more active in vivo than Bestatin as aminopeptidase inhibitor on analgesia induced by methionine-enkephalin.

In particular, the compounds of formula I are active also when administered by intravenous route (see table 2) due to their ability to pass the blood-brain barrier. As shown in table 2 Bestatin is practically inactive when administered by intravenous route.

EXAMPLE 21

Evaluation of the immunostimulating activity

The immunostimulating effect of the compounds of formula I was evaluated as ability to stimulate the incorporation of $^3$H-timidine ($^3$H-TMD) in a culture of mouse splenic lymphocytes. The splenic cells were drawn from C3H/H2 mice (age: 6-8 weeks) and suspended in RPMI-1640 medium containing HEPES 20 mM and 10% bovine fetal serum (inactivated to heat) at the concentration of $5 \times 10^6$ cells/ml. Cells were sowed on Microtest plates (Falcon 3072) in the absence and in the presence of different concentrations of the compounds of formula I and of Bestatin in a volume of 0.2 ml of medium.

After an incubation period of 48 hours at 37° C. in humidified environment at 5% $CO_2/O_2$, 0.5 microCi of $^3$H-TMD (specific activity 2 Ci/mmoles) were added and the incubation was protracted for further 24 hours.

Cells were collected by filtration (Tretertek Cell Harnester) and the incorporated radioactivity was measured by Packard TRI-CARB 4530 scintillator.

The mitogenetic effect was expressed as percentage increase in the incorporation of $^3$H-TMD in lymphocytes incubated with the compounds of formula I and Bestatin at the concentration of 1 uM with respect to the basal incorporation value.

TABLE 1

Potentiation of the analgesic effect of Methionine-enkephalin (Met-enk) after intracerebroventricular administration of Compound 5, Compound 4 and Bestatin.

| Product | Doses μmoles i.c.v. | Reaction time areas | | | |
|---|---|---|---|---|---|
| | | Vehicle | Product | Met-enk | Product Met-enk |
| Compound 5 | 0.16 | 163 ± 11.0 | 156 ± 8.6 | 207 ± 15.6 | 360 ± 19.1 |
| Compound 4 | 0.16 | 151 ± 4.7 | 179 ± 9.9 | 173 ± 11.2 | 290 ± 17.1 |
| Bestatin | 0.16 | 181 ± 6.0 | 222 ± 13.3 | 188 ± 4.7 | 268 ± 11.3 |

Then the compounds of formula I and Bestatin were tested after intravenous (i.v.) administration to study their diffusion across blood-brain barrier.

The administration i.v. of the compounds of formula I and of Bestatin was simultaneous to methionine-enkephalin administration i.c.v.

In table 2 the results obtained for some representative compounds of formula I in comparison with Bestatin are reported.

The compounds of formula I showed a mitogenetic activity at least equal to that of Bestatin.

What we claim is:

1. A compound of formula I

TABLE 2

Potentiation of the analgesic effect of Methionine-enkephalin (Met-enk) after intravenous administration of Compound 5, Compound 2 and Bestatin.

| Product | Doses mmoles/kg i.v. | Reaction time areas | | | |
|---|---|---|---|---|---|
| | | Vehicle | Product | Met-enk | Product Met-enk |
| Compound 5 | 0.16 | 155 ± 5.5 | 150 ± 4.5 | 199 ± 14.0 | 241 ± 17.9 |
| | 0.13 | 150 ± 4.2 | 154 ± 5.7 | 197 ± 16.7 | 299 ± 16.2 |
| Compound 2 | 0.05 | 193 ± 6.0 | 190 ± 7.8 | 208 ± 8.3 | 243 ± 15.9 |
| | 0.08 | 200 ± 11.6 | 191 ± 8.5 | 197 ± 917 | 233 ± 10.1 |
| Bestatin | 0.05 | 170 ± 6.7 | 173 ± 3.7 | 200 ± 6.1 | 202 ± 6.9 |
| | 0.08 | 200 ± 11.6 | 182 ± 8.3 | 197 ± 9.7 | 212 ± 10.0 |

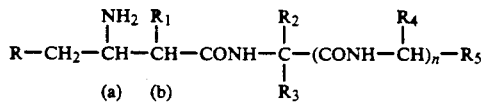

wherein:
- R represents phenyl optionally substituted by a substituent selected from the group consisting of hydroxy, chlorine, bromine, fluorine, methoxy, ethoxy, ethyl, methyl, isopropyl, isobutyl, isopropoxy, isobutoxy, amino, nitro, phenyl, mercapto, methylthio, methylsulfinyl and methylsulfonyl;
- $R_1$ represents hydroxy;
- $R_2$ represents methyl, ethyl, propyl, isopropyl, butyl, isobutyl, or sec.butyl;
- $R_3$ represents methyl, ethyl, propyl, isopropyl, butyl, isobutyl, sec.butyl, hydroxymethyl, hydroxyethyl, mercaptomethyl, or methylthioethyl or
- $R_2$ and $R_3$, together with the carbon atom to which they are bonded, are a cyclopropylidene, cyclobutylidene, cyclopentylidene, or cyclohexylidene;
- $R_4$ represents hydrogen or a linear or branched $C_1$-$C_6$ alkyl optionally substituted by hydroxy, mercapto, $C_1$-$C_3$ alkythio, amino, carboxy or ureido;
- n is 0;
- $R_5$ represents carboxy; and the carbon atoms marked by (a) and (b) are in R or S configuration.

2. A salt of a compound according to claim 1 with pharmaceutically acceptable acids or with pharmaceutically acceptable bases.

3. A compound according to claim 1, wherein the carbon atom marked by (b) is in S configuration.

4. A compound according to claim 1, wherein the carbon atom marked by (b) is in R configuration.

5. A compound according claim 1, wherein the carbon atoms marked by (a) and (b) are in R and S configuration respectively.

6. A pharmaceutical composition containing a compound according to claim 1, as active ingredient and a carrier suitable for pharmaceutical use.

7. A compound according to claim 5, wherein the carbon atom marked by (b) is in S configuration.

8. A compound according to claim 2 wherein the carbon atom marked by (b) is in R configuration.

9. A compound according to claim 2 wherein the carbon atoms marked by (a) and (b) are in R and S configuration respectively.

* * * * *